(12) United States Patent
Chang et al.

(10) Patent No.: US 7,858,662 B2
(45) Date of Patent: Dec. 28, 2010

(54) MEDICAMENT FOR THE TREATMENT OF VIRAL SKIN AND TUMOUR DISEASES

(75) Inventors: Yunik Chang, Sonoma, CA (US); Robert Lathrop, Fort Collins, CO (US); Erwin Böhm, Ladenburg (DE); Irene Gander-Meisterernst, Stockdorf (DE); Regina Greger, Iffeldorf (DE); Johanna Holldack, Ebeltoft (DK); Ulrich Moebius, Gauting-Unterbrunn (DE)

(73) Assignee: MediGene AG, Planegg (DE)

( * ) Notice: Subject to any disclaimer, the term of this patent is extended or adjusted under 35 U.S.C. 154(b) by 1414 days.

(21) Appl. No.: 10/495,889

(22) PCT Filed: Nov. 18, 2002

(86) PCT No.: PCT/EP02/12919

§ 371 (c)(1),
(2), (4) Date: Sep. 24, 2004

(87) PCT Pub. No.: WO03/043628

PCT Pub. Date: May 30, 2003

(65) Prior Publication Data

US 2005/0032895 A1    Feb. 10, 2005

Related U.S. Application Data

(60) Provisional application No. 60/331,705, filed on Nov. 19, 2001.

(30) Foreign Application Priority Data

Nov. 19, 2001   (DE) ................... 101 56 794

(51) Int. Cl.
| | | |
|---|---|---|
| *A61K 31/20* | (2006.01) | |
| *A61K 31/12* | (2006.01) | |
| *A61K 31/35* | (2006.01) | |
| *A61P 15/00* | (2006.01) | |

(52) U.S. Cl. ............... 514/558; 514/675; 514/560; 514/546; 514/934; 514/947; 514/967; 514/969; 514/453; 514/732

(58) Field of Classification Search ............ 514/934, 514/947, 967, 969
See application file for complete search history.

(56) References Cited

U.S. PATENT DOCUMENTS

| | | |
|---|---|---|
| 4,002,775 A | 1/1977 | Kabara |
| 4,248,789 A | 2/1981 | Okada |
| 4,613,672 A | 9/1986 | Hara |
| 4,673,530 A | 6/1987 | Hara |
| 4,863,970 A * | 9/1989 | Patel et al. .......... 514/784 |
| 4,913,909 A | 4/1990 | Hara et al. |
| 4,931,284 A | 6/1990 | Ekman et al. |
| 5,104,901 A | 4/1992 | Shimamura et al. |
| 5,135,957 A | 8/1992 | Shimamura |
| 5,137,922 A | 8/1992 | Shimamura et al. |
| 5,204,089 A | 4/1993 | Hara et al. |
| 5,306,486 A | 4/1994 | McCook et al. |
| 5,318,986 A | 6/1994 | Hara et al. |
| 5,358,713 A | 10/1994 | Shimamura |
| 5,470,565 A | 11/1995 | Hayakawa et al. |
| 5,633,284 A | 5/1997 | Meyer |
| 5,652,266 A | 7/1997 | Bobier-Rival et al. |
| 5,670,154 A | 9/1997 | Hara et al. |
| 5,747,053 A | 5/1998 | Nashimoto et al. |
| 5,766,595 A | 6/1998 | Yamane et al. |

(Continued)

FOREIGN PATENT DOCUMENTS

DE   199 62 369   6/2001

(Continued)

OTHER PUBLICATIONS

Chemical Abstracts (1974), vol. 80, No. 4, p. 319.

(Continued)

*Primary Examiner*—Shengjun Wang
*Assistant Examiner*—Sahar Javanmard
(74) *Attorney, Agent, or Firm*—Karen L. Elbing; Clark & Elbing LLP

(57) ABSTRACT

The invention relates to a medicament containing a compound of general formula (1), where $R_1$=independently, a straight or branched, saturated, singly- or multiply-unsaturated, optionally substituted $C_{11}$-$C_{21}$ alkyl, alkylene or alkynyl group, preferably a $C_{11}$-$C_{15}$ alkyl, alkylene or alkynyl group, particularly a $C_{11}$-$C_{13}$ alkyl, alkylene or alkynyl group, most preferably a $C_{13}$ alkyl group, R2=independently, a straight or branched $C_1$-$C_8$ alkyl, alkylene or alkynyl group, preferably a $C_1$-$C_6$ alkyl, alkylene or alkynyl group, in particular a $C_2$-$C_4$ alkyl, alkylene or alkynyl group, most preferably a $C_3$ alkyl group, a —[$CH_2$—($CH_2$)$_m$—O]$_n$H group with n=1 to 10, preferably n=1 to 5, m=1 to 5, preferably m=1 to 3, a —$CH_2$—[CH—(OH)]$_p$[$CH_2$—($R_3$)]— group, where $R_3$=independent H or OH, p=1 to 7, preferably p=1 to 4, a pentose group or a hexose group, as therapeutically active agent, alone or in combination with one or several further pharmaceutical agents as a combination preparation for the treatment of viral skin diseases and/or tumor diseases, in particular caused by human papilloma virus (HPV) and/or herpes viruses and a topically acting medicament formulation and the use thereof.

(I)

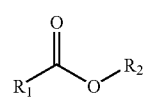

25 Claims, No Drawings

U.S. PATENT DOCUMENTS

| | | | |
|---|---|---|---|
| 5,795,911 | A | 8/1998 | Cheng et al. |
| 5,804,567 | A | 9/1998 | Cheng et al. |
| 5,807,564 | A | 9/1998 | Shimamura et al. |
| 5,888,527 | A | 3/1999 | Nashimoto et al. |
| 5,910,308 | A | 6/1999 | D'Jang |
| 5,968,973 | A | 10/1999 | Cheng et al. |
| 6,096,359 | A | 8/2000 | Bombardelli et al. |
| 6,127,393 | A * | 10/2000 | Fernandez-Pol ............ 514/354 |
| 6,197,808 | B1 | 3/2001 | Cheng et al. |
| 6,210,679 | B1 | 4/2001 | Bailey et al. |
| 6,248,346 | B1 | 6/2001 | Hara et al. |
| 6,337,320 | B1 | 1/2002 | Hersh et al. |
| 6,372,234 | B1 | 4/2002 | Deckers et al. |
| 6,399,046 | B1 | 6/2002 | Schonrock et al. |
| 6,576,660 | B1 | 6/2003 | Liao et al. |
| 6,596,763 | B1 | 7/2003 | Thormar et al. |
| 6,696,484 | B2 | 2/2004 | Liao et al. |
| 6,723,750 | B2 | 4/2004 | Voet |
| 2002/0006447 | A1 | 1/2002 | Yamazaki et al. |
| 2002/0031535 | A1 | 3/2002 | Sheffield |
| 2002/0151582 | A1 | 10/2002 | Dou et al. |
| 2002/0198161 | A1 | 12/2002 | Brash et al. |
| 2003/0143165 | A1 | 7/2003 | Evans et al. |
| 2003/0166583 | A1 | 9/2003 | Yoa-Pu Hu et al. |
| 2004/0181130 | A1 | 9/2004 | Miller et al. |
| 2004/0191842 | A1 | 9/2004 | Hsu et al. |
| 2005/0079235 | A1 | 4/2005 | Stockfleth |
| 2007/0059387 | A1 | 3/2007 | Stockfleth |

FOREIGN PATENT DOCUMENTS

| | | |
|---|---|---|
| EP | 0 087 161 | 8/1983 |
| EP | 0 224 457 | 6/1987 |
| EP | 0 573 682 | 12/1993 |
| EP | 0 842 660 A1 | 5/1998 |
| EP | 1 005 862 A1 | 6/2000 |
| WO | WO 98/20872 | 5/1998 |
| WO | WO 99/66897 | 12/1999 |
| WO | WO 00/29027 | 5/2000 |
| WO | WO 00/33832 | 6/2000 |
| WO | WO 2001/051048 | 7/2001 |
| WO | WO 2004/026323 | 4/2004 |
| WO | WO 2004/053097 | 6/2004 |

OTHER PUBLICATIONS

Garg S. et al., "Compendium of Pharmaceutical Excipients for Vaginal Formulations," *Pharmaceutical Technology Drug Delivery* pp. 14-24 (2001).

CIR Compendium 1995, p. 88 (Abstract).

Beutner et al. "Treatment of Genital Warts with an Immune-Response Modifier (Imiquimod)," *Journal of the American Academy of Dermatology* 38:230-239 (1998).

Ceve, "Drug Delivery Across the Skin," *Exp. Opin. Invest. Drugs* 6:1887-1937 (1997).

Diding et al., "Isopropyl Myristate as Solvent in Sterility Testing of Petrolatum-Based Ointments," pp. 616-621 (Chemical Abstract 19503q) (1973).

Edwards et al., "Self-Administered Topical 5% Imiquimod Cream for External Anogenital Warts," *Arch. Dermatol.* 134:25-30 (1998).

Kristmundsdottir et al., "Development and Evaluation of Microbicidal Hydrogels Containing Monoglyceride as the Active Ingredient," *Journal of Pharmaceutical Sciences* 88:1011-1015 (1999).

Sands et al., "Extreme Sensitivity of Enveloped Viruses, Including Herpes Simplex, to Long-Chain Unsaturated Monoglycerides and Alcohols," *Antimicrobial Agents and Chemotherapy* 15:67-73(1979).

Handbook of Pharmaceutical Excipients, published by (1986) American Pharmaceutical Association and the Pharmaceutical Society of Great Britain pp. 148.

Beutner et al., "Patient-Applied Podofilox for Treatment of Genital Warts," *The Lancet* 1:831-834 (1989).

Greenberg et al., "A Double-Blind, Randomized Trial of 0.5% Podofilox and Placebo for the Treatment of Genital Warts in Women," *Obstet Gynecol.* 77:735-739 (1991).

Hara, "Antioxidants in Tea and Their Physiological Functions," *Food and Free Radicals* (edited by Hiramatsu et al.), Plenum Press (New York), pp. 49-65 (1997).

Kirby et al., "Double-Blind Randomized Clinical Trial of Self-Administered Podofilox Solution Versus Vehicle in the Treatment of Genital Warts," *Am J Med.* 88:465-469 (1990).

Miura et al., "Effects of Various Natural Antioxidants on the $Cu^{2+}$-Mediated Oxidative Modification of Low Density Lipoprotein," *Biol Pharma Bull* 18:1-4 (1995).

Mukoyama et al., "Inhibition of Rotavirus and Enterovirus Infections by Tea Extracts," *Jpn J Med Sci Biol.* 44:181-186 (1991).

Nakayama et al., "Inhibition of the Infectivity of Influenza Virus by Tea Polyphenols," *Antivir Res.* 21:289-299 (1993).

Rice-Evans et al., "The Relative Antioxidant Activities of Plant-Derived Polyphenolic Flavonoids," *Free Rad Res.* 22:375-383 (1995).

Rösl et al., "Antioxidant-Induced Changes of the AP-1 Transcription Complex are Paralleled by a Selective Suppression of Human Papillomavirus Transcription," *J Virol.* 71:362-370 (1997).

Toda et al., "Antibacterial and Anti-Hemolysin Activities of Tea Catechins and Their Structural Relatives," *Jpn J Bacteriol.* 45:561-566 (1990). Abstract only.

Toda et al., "The Bactericidal Activity of Tea and Coffee," *Lett Appl Microbiol.* 8:123-125 (1989).

Tomita et al., "Tea and Its Components as Powerful Antioxidants," *Oxidative Stress and Aging* (edited by Cutler et al.), Birkhäuser Verlag (Basel, Switzerland), pp. 355-365 (1995).

Tyring et al., "Safety and Efficacy of 0.5% Podofilox Gel in the Treatment of Anogenital Warts," *Arch Dermatol.* 134:33-38 (1998).

Database STN Chemical Abstracts (XP-002123681) (1995).

European Search Report for EP 08 02 1728, dated Mar. 26, 2010.

Perry et al., "Topical Imiquimod: A Review of its Use in Genital Warts, " *Drugs* 58(2): 375-390 (1999).

Ahmad et al., "Green tea constituent epigallocatechin-3-gallate and induction of apoptosis and cell cycle arrest in human carcinoma cells," *Journal of the National Cancer Institute* 89: 1881-1886 (1997).

An et al., "Cyclooxygenase-2 expression in murine and human nonmelanoma skin cancers: implications for therapeutic approaches," *Photochemistry and Photobiology* 76: 73-80 (2002).

Araki et al., "Chemoprevention of mammary preneoplasia. In vitro effects of a green tea polyphenol," *Annals of the New York Academy of Sciences* 768: 215-222 (1995).

Bickers and Athar, "Novel approaches to chemoprevention of skin cancer," *The Journal of Dermatology* 27: 691695 (2000).

Cao et al., "Angiogenesis inhibited by drinking tea," *Nature* 398: 381 (1999).

Carter et al., "Drug-tumor interactions," *Chemotherapy of Cancer* (Second Edition), pp. 361-379 (1981).

Jia et al., "Effects of tea on preneoplastic lesions and cell cycle regulators in rat liver," *Cancer Epidemiology, Biomarkers & Prevention* 11: 1663-1667 (2002).

Katiyar et al., "Green tea and skin," *Archives of Dermatology* 136: 989-994 (2000).

Katiyar et al., "Protection against induction of mouse skin papillomas with low and high risk of conversion to malignancy by green tea polyphenols," *Carcinogenesis* 18: 497-502 (1997).

Li et al., "The chemopreventive effects of tea on human oral precancerous mucosa lesions," *Proceedings of the Society for Experimental Biology and Medicine* 220: 218-224 (1999).

Linden et al., "Chemoprevention of nonmelanoma skin cancer: experience with a polyphenol from green tea," *Recent Results in Cancer Research* 163: 165-171 (2003).

Linden et al., "Chemoprevention of non-melanoma skin cancer: experience with a polyphenol from green tea," *European Journal of Cancer* 38: S24 (2002).

Linden et al., "Epigallocatechin gallate in the chemoprevention of non-melanoma skin cancer, with biomarker studies of actinic keratoses, sun-damaged, and non sun-damaged skin: results of a clinical trial," Poster Session A: Behavioral Science, Survivorship Research, and Science and Public Policy: Frontiers in Cancer Prevention Research (Abstract A113).

McCarty, "Polyphenol-mediated inhibition of AP-1 transactivating activity may slow cancer growth by impeding angiogenesis and tumor invasiveness," *Medical Hypothesis* 50: 511-514 (1998).

Mukhtar et al., "Green tea in chemoprevention of cancer," *Toxicological Sciences* 52: 111-117 (1999).

Mukhtar et al., "Green tea polyphenols induce apoptosis and alter the progression of cell cycle in human epidermoid carcinoma cells," Proceedings of the American Association for Cancer Research and American Society of Clinical Oncology 38: 580 (1997).

Office Action for U.S. Appl. No. 10/574,422, mailed on Nov. 20, 2009.
Office Action for U.S. Appl. No. 10/574,422 mailed on Jun. 29, 2009.
Office Action for U.S. Appl. No. 10/574,422 mailed on Dec. 8, 2008.
Office Action for U.S. Appl. No. 10/574,422 mailed on Jun. 17, 2008.
Office Action for U.S. Appl. No. 10/574,422 mailed on Dec. 18, 2007.
Office Action for U.S. Appl. No. 10/574,422 mailed on Jul. 6, 2007.
Office Action for U.S. Appl. No. 10/682,612 mailed on Jul. 7, 2009.
Office Action for U.S. Appl. No. 10/682,612 mailed on Oct. 21, 2008.
Office Action for U.S. Appl. No. 10/682,612 mailed on Jan. 30, 2008.
Office Action for U.S. Appl. No. 10/682,612 mailed on Aug. 3, 2007.
Office Action for U.S. Appl. No. 10/682,612 mailed on Jan. 29, 2007.
Office Action for U.S. Appl. No. 10/682,612 mailed on Jul. 28, 2006.

Pillai et al., "Antimutagenic/antioxidant activity of green tea components and related compounds," *Journal of Environmental Pathology, Toxicology, and Oncology* 18: 147-158 (1999). (Abstract).

Proniuk et al., "Preformulation study of epigallocatechin gallate, a promising antioxidant for topical skin cancer prevention," *Journal of Pharmaceutical Sciences* 91: 111-116 (2002).

Wang et al., "Inhibitory effects of black tea, green tea, decaffeinated black tea, and decaffeinated green tea on ultraviolet B light-induced skin carcinogenesis in 7,12-dimethylbenz[$\alpha$]anthracene-initiated SKH-1 mice," *Cancer Research* 54: 3428-3435 (1994).

Yanaga et al., "Prevention of carcinogenesis of mouse mammary epithelial cells RIII/MG by epigallocatechin gallate," *International Journal of Molecular Medicine* 10: 311-315 (2002).

Zhao et al., "Photoprotection in human skin by green tea and black tea," *Proceedings of the American Association for Cancer Research* 39: 382 (1998).

Zhao et al., "Photoprotective effect of black tea extracts against UVB-induced phototoxicity in skin," *Photochemistry and Photobiology* 70: 637-644 (1999).

Zhu et al., "Study of tea polyphenol as a reversal agent for carcinoma cell lines' multidrug resistance (study of TP as a MDR reversal agent)," *Nuclear Medicine and Biology* 28: 735-740 (2001).

\* cited by examiner

MEDICAMENT FOR THE TREATMENT OF VIRAL SKIN AND TUMOUR DISEASES

CROSS REFERENCE TO RELATED APPLICATIONS

This application is the U.S. National Stage of International Application No. PCT/EP02/12919, filed Nov. 18, 2002, which claims benefit of German Patent Application No. 10156794.4 filed Nov. 19, 2001, and 60/331,705, filed Nov. 19, 2001.

The present invention relates to a pharmaceutical which comprises a compound of the formula

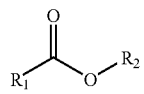

where $R_1$, independent of each other, is an unbranched or branched, saturated, singly or multiply unsaturated, optionally substituted $C_{11}$-$C_{21}$ alkyl, alkylene or alkynyl radical, preferably a $C_{11}$-$C_{15}$ alkyl, alkylene or alkynyl radical, in particular a $C_{11}$-$C_{13}$ alkyl, alkylene or alkynyl radical, especially a $C_{13}$-alkyl radical, and $R_2$ is, independent of each other, an unbranched or branched $C_1$-$C_8$ alkyl, alkylene or alkynyl radical, preferably a $C_1$-$C_6$ alkyl, alkylene or alkynyl radical, in particular a $C_2$-$C_4$ alkyl, alkylene or alkynyl radical, especially a $C_3$-alkyl radical, a —[$CH_2$—($CH_2$)$_m$—O]$_n$—H radical where n=1 to 10, preferably n=1 to 5, m=1 to 5, preferably m=1 to 3, a —$CH_2$—[CH—(OH)]$_p$—($CH_2$—($R_3$))] radical, where $R_3$ is, independent of each other, a hydrogen or a hydroxyl radical, p=1 to 7, preferably p=1 to 4, a pentose radical or a hexose radical, as a therapeutically active compound, either alone or together with one or more additional pharmaceutical active compounds as a combination preparation, for treating viral skin diseases and/or tumor diseases which are caused, in particular, by human papilloma viruses (HPV) and/or herpes viruses, and also to a topically acting pharmaceutical formulation and its use.

Papilloma viruses (HPV) are DNA viruses which infect the epithelial cells of mammals and thereby induce uncontrolled cell growth. There are a very wide variety of papilloma viruses, which infect humans and different animal species. In this connection, all the viral types infect the basal epithelial cells and remain as episomes or integrate their DNA into the host genome.

It has been known for a long time that papilloma viruses cause genital warts (Condyloma acuminata), ordinary and plantar warts, bowenoid papulosis in men and women, and cervical intraepithelial neoplasias in women.

Depending on the method used, the detection rate for HPV is almost 100%. It is in the main HPV 6 and HPV 11 viruses which are found in warts and genital warts (Condyloma acuminata). Since HPV 16 and HPV 18 are principally observed in malignant, desquamative cell carcinomas, as in the case of cancer of the penis and of the uterine cervix, it is generally accepted that HPV 16 and HPV 18 are linked to malignant HPV diseases.

At present, physical methods are predominantly used for treating genital warts caused by human papilloma viruses. These methods include surgical removal, electrocauterization, cryosurgery and laser therapy to mention but a few. An additional medicinal treatment is the use of Podophyllin, 5-Fluorouracil, Bleomycin, Interferon, Imiquimod, etc.

Surgical treatment suffers from the disadvantage that it is very unpleasant for the patient and can lead to further infection. Up until now, a topical use has involved the risk of side effects since the active compounds employed possess cytotoxic properties or augment the cellular immune defense and can consequently induce local inflammations. This demonstrates that the therapeutic possibilities which have thus far been available are still not satisfactory.

In addition to this, there is the fact that the proportion of recurrences is very high in the case of warts and genital warts and complete healing can only be achieved by means of constant and consistent treatment. For this reason, there is a need for a more reliable and comfortable treatment.

Particularly when treating genital warts, but also in connection with all the other diseases which are caused by the papilloma virus, there is a requirement for a treatment which is easy for the patient to use. For example, a treatment which the patient himself can use at the affected sites and which gives good results in relatively short time, and exhibits only few or no side effects, would be suitable.

Herpes simplex viruses (HSV) are DNA viruses from the alpha subfamily Herpetoviridae. They are divided into two groups, i.e. HSV 1, termed the oral strain, and HSV 2, termed the genital strain. Herpes simplex viruses penetrate, as a nucleocapsid, into the nerve endings and, using the axonal flow, reach the appurtenant ganglia. They are transmitted by smear and droplet infection from herpes lesions or by healthy chronic carriers. Following a primary infection, the viruses can be reactivated once again, symptomatically or a symptomatically, by irritation, for example due to fever, trauma or radiation, of latently infected neurons. This reactivation depends, in particular, on the defensive condition of the body taken as a whole. Herpes simplex viruses can transform cells neoplastically in animals and in cell cultures. The possibility of an interaction between type 2 herpes simplex viruses and the genesis of cervical carcinomas involving type 16 and type 18 human papilloma viruses is presently being discussed.

EP 0 087 161 discloses treating herpes infections by treating them with a mixture consisting of isopropyl myristate and small quantities of 4-{lower alkyl}-2,6-(bis-tert-butyl)phenol containing 2,6-(bis-tert-butyl)-4-hydroxytoluene or 4-(lower alkyl)-2,6-(bis-tert-butyl)phenol.

EP 0 842 660 describes a pharmaceutical composition for treating genital warts which are caused by human papilloma viruses. The composition which is described comprises catechols from tea extracts (*Camellia sinensis*), predominantly (–)-epigallocatechol-gallate in the form of an ointment or a suppository.

An object of the present invention is therefore to find additional effective antiviral substances and formulations which are suitable for treating viral skin diseases and/or tumor diseases which are caused by papilloma viruses and/or herpes viruses.

It has now been found, surprisingly, that a pharmaceutical which comprises a compound according to the invention of the formula (I) as the pharmaceutically active compound is suitable for treating viral skin diseases and/or tumor diseases.

The present invention consequently relates to a pharmaceutical which comprises a compound of the formula (I) as the pharmaceutically active compound, where A is a radical of the formula (II)

(II)

and B is a radical of the formula (III)

and $R_1$ is, independent of each other, an unbranched or branched, saturated, singly or multiply unsaturated, optionally substituted $C_{11}$-$C_{21}$ alkyl, alkylene or alkynyl radical, preferably a $C_{11}$-$C_{15}$ alkyl, alkylene or alkynyl radical, in particular a $C_{11}$-$C_{13}$ alkyl, alkylene or alkynyl radical, especially a $C_{13}$-alkyl radical, and $R_2$ is, independent of each other, an unbranched or branched $C_1$-$C_8$ alkyl alkylene or alkynyl radical, preferably a $C_1$-$C_6$ alkyl, alkylene or alkynyl radical, in particular a $C_2$-$C_4$ alkyl, alkylene or alkynyl radical, especially a $C_3$ alkyl radical, a —$[CH_2$—$(CH_2)_m$—$O]_n$—H radical where n=1 to 10, preferably n=1 to 5, m=1 to 5, preferably m=1 to 3, a —$CH_2$—$[CH$—$(OH)]_p$—$(CH_2$—$(R_3)]$ radical, where $R_3$ is, independent of each other, a hydrogen or a hydroxyl radical, p=1 to 7, preferably p=1 to 4, a pentose radical or a hexose radical.

In this connection, the radical $R_1$ and/or the radical $R_2$ can, independent of each other, be substituted by a halogen, preferably fluorine and/or chlorine, or an unbranched or branched $C_1$-$C_6$ alkyl, alkylene or alkynyl radical, preferably a $C_1$-$C_3$ alkyl, alkylene or alkynyl radical, in particular a methyl radical.

In this connection, the radical A of the compound (I) can, for example, be derived from hexanoic acid (caproic acid), heptanoic acid, octanoic acid (caprylic acid), nonanoic acid, decanoic acid (capric acid), undecanoic acid, dodecanoic acid (lauric acid), tridecanoic acid, tetradecanoic acid (myristic acid), pentadecanoic acid, hexadecanoic acid (palmitic acid), heptadecanoic acid, octadecanoic acid (stearic acid), nonadecanoic acid, eicosanoic acid, heneicosanoic acid, oleic acid, linoleic acid, linolenic acid and/or arachidonic acid, preferably from caproic acid, caprylic acid, capric acid, lauric acid, myristic acid, palmitic acid, stearic acid, oleic acid, linoleic acid, linolenic acid and/or arachidonic acid, particularly preferably from myristic acid.

The radical B of the compound (I) can, for example, be derived from an unbranched or branched $C_1$-$C_8$ alkyl alcohol, in particular ethanol, propanol, isopropanol, n-butanol, tert-butanol, particularly preferably isopropanol, ethylene glycol, polyethylene glycol, propylene glycol, polypropylene glycol, glycerol, polyglycerol, a pentose sugar, such as arabitol, adonitol and xylitol, or a hexose sugar, such as sorbitol, mannitol or dulcitol, preferably from ethanol, propanol, isopropanol, butanol, ethylene glycol, polyethylene glycol, propylene glycol, polypropylene glycol, glycerol, polyglycerol, arabitol, adonitol, xylitol, sorbitol, mannitol and/or dulcitol.

The compound (I) is preferably isopropyl laureate, isopropyl myristate, isopropyl palmitate, isopropyl stearate, ethyl myristate, propyl myristate, butyl myristate and/or ethyl oleate, in particular isopropyl myristate.

In another preferred embodiment, the compound (I) is a hydrophobic compound. According to the present invention, a hydrophobic compound is understood as being a compound whose solubility in water is at most approx. 0.2 mg/ml, in particular at most approx. 0.1 mg/ml.

The pharmaceutical comprises, for example, at least approx. 5%-75% (w/w), preferably at least approx. 10%-60% (w/w), in particular at least approx. 25%-55% (w/w), and especially at least approx. 35%-50% (w/w) of the compound of the formula (I).

In this connection, the pharmaceutical according to the invention can also contain one or more additional pharmaceutical active compounds as a combination preparation for use which is simultaneous, separate or staggered in time. In this context, preference is given to employing, as additional pharmaceutical active compounds, those compounds which can be used for treating viral skin diseases and/or tumor diseases, such as podophyllin, 5-fluorouracil, bleomycin, interferon or imiquimod, and/or mixtures which comprise at least one catechol.

In a preferred embodiment, the additional pharmaceutical active compound is an amphiphilic or amphipathic active compound. An amphiphilic or amphipathic active compound is understood as being an active compound which is composed of two functional moieties, in particular one hydrophilic moiety and one lipophilic moiety. This property might, in particular, be able to facilitate the passage of the substance through the skin and achieve an improved effect. In this connection, the improved effect may be attributable, for example, to a longer dwell time at the desired site or to a reduction in the dose of the active compound.

In a further preferred embodiment, the additional pharmaceutical active compound comprises at least one catechol of the formula (IV)

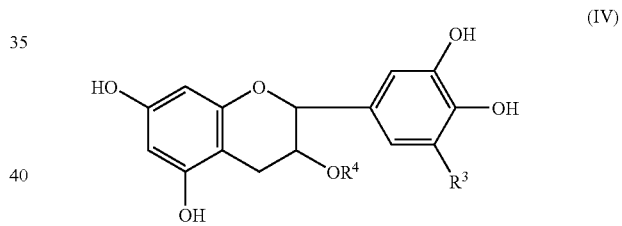
(IV)

in which $R_3$ is —H or —OH, and $R_4$ is —H or a group of the formula (V)

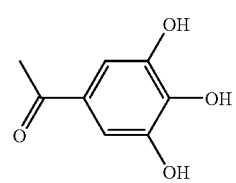
(V)

The catechols which are added in this connection may be obtained either synthetically or from natural sources. The natural sources which may especially be mentioned are tea plants. In this context, the natural constituents may be present in differing concentrations depending on the species and variety. In this connection, the catechols which are employed are preferably isolated from *Camellia sinensis, Camellia asamica, Camellia bohea, Camellia chinensis* or *Camellia oleosa*. All the components of tea plants, in particular the leaves, can be used for isolating the catechols. The catechols which are employed are preferably isolated from a tea extract.

The catechols which are employed in the present invention are preferably epicatechol, epicatechol gallate, epigallocatechol, epigallocatechol gallate, gallocatechol and gallocatechol gallate, in particular (−)-epicatechol, (−)-epicatechol gallate, (−)-epigallocatechol, (−)-epigallocatechol gallate, (+)-gallocatechol and (−)-gallocatechol gallate.

The catechols can be used both individually and in the form of mixtures having different compositions. A catechol mixture contains approx. 2-20% (w/w), preferably approx. 4-15% (w/w), in particular approx. 10-11% (w/w) of (−)-epicatechol, approx. 2-20% (w/w), preferably approx. 5-15% (w/w), in particular approx. 5-7% (w/w) of (−)-epicatechol gallate, approx. 1-25% (w/w), preferably approx. 3-15% (w/w), in particular approx. 5-7% (w/w) of (−)-epigallocatechol, approx. 40-75% (w/w), preferably approx. 57-67% (w/w), in particular approx. 61-66% (w/w) of (−)-epigallocatechol gallate, approx. 0.05-5% (w/w), preferably approx. 0.1-1% (w/w), in particular approx. 0.1-0.6% (w/w) of (+)-gallocatechol and/or approx. 0.5-20% (w/w), preferably approx. 1-10% (w/w), in particular approx. 1-5% (w/w) of (−)-gallocatechol gallate.

In a preferred embodiment, the catechol mixture is composed of approx. 5.9% (w/w) of (−)-epicatechol, approx. 12.6% (w/w) of (−)-epicatechol gallate, approx. 17.6% (w/w) of (−)-epigallocatechol, approx. 53.9% (w/w) of (−)-epigallocatechol gallate and/or approx. 1.4% (w/w) of (−)-gallocatechol. A composition of this nature is known under the name Polyphenon® 100.

In a particularly preferred embodiment, the catechol mixture is composed of approx. 10.8% (w/w) of (−)-epicatechol, approx. 6.5% (w/w) of (−)-epicatechol gallate, approx. 9.2% (w/w) of (−)-epigallocatechol, approx. 54.8% (w/w) of (−)-epigallocatechol gallate and/or approx. 4.0% (w/w) of (−)-gallocatechol gallate. A composition of this nature is known under the name Polyphenon® E.

The pharmaceutical according to the invention comprises, for example, approx. 1-30% (w/w), preferably approx. 2-20% (w/w) and, in particular, approx. 15-18% (w/w) of a catechol and at least approx. 5-90% (w/w), preferably at least approx. 10-70% (w/w), in particular at least approx. 25-60% (w/w) and, especially, at least approx. 35-50% (w/w) of the compound (I).

The familiar methods of pharmaceutical technology are used, in a customary manner, for preparing pharmaceuticals which comprise one or more compounds according to the invention and/or for using these pharmaceuticals in the application according to the invention. For this, the active compounds are worked up, together with suitable, pharmaceutically acceptable auxiliary substances and carrier substances, into the medicinal forms which are suitable for the different indications and sites of administration. In this context, the pharmaceuticals can be prepared such that the rate of release in each case desired, for example a rapid accumulation and/or a delayed-release or depot effect, is achieved.

Customary emulsions, gels, ointments, creams of the mixed-phase or amphiphilic emulsion systems (oil/water-water/oil mixed phase), and also liposomes and transfersomes or plasters, preferably ointments and creams, particularly preferably an ointment, may be mentioned for conventional application to the skin or mucosa. The active compound is preferably applied locally in the region in which there is a skin or mucosal change and/or disease.

In addition to the known uses on the skin and/or mucosa, the following are suitable for use as special pharmaceutical preparations which can be administered topically, locally or regionally: emulsions, creams, ointments, effervescent tablets or suppositories which can be administered genitally, vaginally or rectally, in particular genitally and vaginally. Rectal capsules can also be prepared on the basis of gelatin or other carrier substances. Suitable suppository bases are hardened fats, such as Witepsol®, Massa Estarium®, Novata®, coconut butter, glycerol/gelatin pastes, glycerol/soap gels and polyethylene glycols.

Examples of suitable auxiliary and/or carrier substances are sodium alginate, as a gelatinizing agent for preparing a suitable base, or cellulose derivatives, such as guar or xanthan gum, inorganic gelatinizing agents, such as aluminum hydroxide or bentonites (what are termed thixotropic gel-formers), polyacrylic acid derivatives, such as Carbopol®, polyvinylpyrrolidone, microcrystalline cellulose and carboxymethylcellulose. Amphiphilic low molecular weight and higher molecular weight compounds, and also phospholipids, are also suitable. The gels can be present either as water-based hydrogels or as hydrophobic organogels, for example based on mixtures of low and high molecular weight paraffin hydrocarbons and vaseline. The hydrophilic organogels can be prepared, for example, on the basis of high molecular weight polyethylene glycols. These gelatinous forms are washable. However, the organogels which are preferred are the hydrophobic organogels. Particular preference is given to hydrophobic auxiliary substances and additives, such as petroleum jelly, wax, oleyl alcohol, propylene glycol monostearate and propylene glycol monopalmitostearate. It is, of course, likewise possible to add skin-sedating and/or inflammation-inhibiting additives which are known to the skilled person, such as synthetically prepared active compounds and/or extracts and/or active compounds from medicinal plants, in particular bisobolol and panthenol. It is furthermore also possible to add dyes, for example yellow and/or red iron oxide and/or titanium dioxide for the purpose of matching as regards color.

Emulsifiers which can be employed are anionic, cationic or neutral surfactants, for example alkali metal soaps, metal soaps, amine soaps, sulfonated compounds, invert soaps, higher fatty alcohols, partial fatty acid esters of sorbitan and polyoxyethylene sorbitan, e.g. lanette types, wool wax, lanolin or other synthetic products for preparing the oil/water and/or water/oil emulsions.

It is possible to use vaseline, natural or synthetic waxes, fatty acids, fatty alcohols, fatty acid esters, for example as monoglycerides, diglycerides or triglycerides, paraffin oil or vegetable oils, hydrogenated castor oil or coconut oil, hog fat, synthetic fats, for example based on, caprylic acid, capric acid, lauric acid or stearic acid, such as Softisan®, or triglyceride mixtures, such as Miglyol®, can be used as lipids, in the form of fatty and/or oleaginous and/or waxy components for preparing the ointments, creams or emulsions.

It is possible to use, for example, osmotically active acids and alkaline solutions, for example hydrochloric acid, citric acid, sodium hydroxide solution, potassium hydroxide solution, sodium hydrogen carbonate, and, in addition, buffer systems, such as citrate, phosphate, tris buffer or triethanolamine, for adjusting the pH. It is possible to add preservatives as well, such as methyl benzoate or propyl benzoate (parabens) or sorbic acid, for increasing the stability.

Pastes, powders and solutions may be mentioned as additional forms which can be applied topically. As consistency-imparting bases, the pastes frequently contain hydrophobic and hydrophilic auxiliary substances, preferably, however, hydrophobic auxiliary substances containing a very high proportion of solids. In order to increase dispersity, and also flowability and slipperiness, and also to prevent agglomerates, the powders or topically applicable powders can, for example, contain starch species, such as wheat or rice starch, flame-dispersed silicon dioxide or siliceous earth, which also serve as diluent.

The medicinal forms which are in each case suitable can be produced on the basis of pharmaceutico-physical principles in conformity with formulation guidelines and methods known to a skilled person.

The pharmaceutical according to the invention preferably comprises approx. 35% (w/w) of isopropyl myristate, approx. 15% (w/w) of at least one catechol, approx. 24.5% (w/w) of petroleum jelly, approx. 20% (w/w) of wax, approx. 5% (w/w) of propylene glycol monostearate or propylene glycol monopalmitostearate and approx. 0.5% (w/w) of oleyl alcohol.

The pharmaceutical of the present invention and/or of a pharmaceutical metabolites is used in the treatment of viral skin diseases and/or tumour diseases.

The term pharmaceutical metabolite is to be understood as meaning one or more compounds which arise during use as a result of biological metabolism. These metabolites can be intermediates arising during intermediary metabolism or the end products of metabolism. The metabolites are preferably metabolic products which arise as a result of application to the skin and/or mucosa, in particular hydrolysis products of the compound having the formula (I). Conceivable hydrolysis products can be derived, for example, from radical A and/or radical B.

Viral skin diseases are understood as being skin diseases which are induced or caused by viruses and/or associated with viral infections. They include, for example, skin diseases such as warts, genital warts, benign tumors of the skin and/or mucosa which are caused by papilloma viruses, for example verrucae plantares, verrucae vulgares, verrucae planae juveniles, epidermodysplasia verruciformis, Condylomata acuminata, Condylomata plana, bowenoid papulosis, papillomas on the larynx and oral mucosa, focal epithelial hyperplasia, herpes labialis, Kaposi's sarcoma, varicella and shingles.

These viral skin diseases and/or tumor diseases are caused by at least one papilloma virus or viruses, in particular human papilloma viruses, such as HPV 1, 2, 3, 4, 5, 6, 8, 9, 11, 12, 13, 14, 15, 16, 17, 18, 19-29, 31, 32, 34, 36-38, 46-50, 56, 58, by at least one herpes virus or herpes viruses, such as herpes simplex virus 1, herpes simplex virus 2, varicella zoster virus, or human herpes virus, such as 1, 2, 3, 4, 7 or 8.

The figures and the following examples are intended to clarify the invention without restricting it. Skilled persons can modify the invention appropriately, within the bounds of customary ability, without departing from the protective scope.

EXAMPLES

Clinical Study for Comparing an Ointment and a Cream Containing Isopropyl Myristate 93 patients (in each case divided equally into men and women) took part in a multicenter clinical study which was carried out at a total of 30 different centers in Germany and Russia. The study was randomized and performed double-blind. The study examined the clinical efficacy of two different formulations of isopropyl myristate (an ointment and a cream) in the treatment of external genital warts.

The formulations which were tested had the following compositions:

Cream 1:

| Substance | Quantity (in % w/w) |
| --- | --- |
| Cera alba | 6.996 |
| Monomuls | 2.798 |
| Lameform TGI | 5.598 |
| Cetiol V | 6.996 |
| Isopropyl myristate | 13.992 |
| Tocopherol | 0.699 |
| Controx KS | 0.066 |
| Glycerol | 6.996 |
| Disodium EDTA | 0.001 |
| Magnesium sulfate | 1.399 |
| D-Panthenol | 0.699 |
| Purified water | 53.678 |
| Red Iron Oxide* | 0.025 |
| Yellow Iron Oxide* | 0.054 |

*The dyes were added for matching as regards color.

Ointment 1:

| Substance | Quantity (in % w/w) |
| --- | --- |
| White Petrolatum, USP | 34.023 |
| White Wax, NF | 25.000 |
| Isopropyl Myristate, NF | 35.000 |
| Oleyl Alcohol, NF | 0.500 |
| Propylene Glycol Monostearate, NF | 5.000 |
| Red Iron Oxide* | 0.022 |
| Yellow Iron Oxide* | 0.055 |
| Titanium Dioxide, USP* | 0.400 |

*The dyes were added for matching as regards color.

The patients applied the topical study medication three times daily or until the genital warts had completely healed or for a maximum of twelve weeks.

The following data were collected during the study:

| | Complete healing (in %) | |
| --- | --- | --- |
| | Cream 1 | Ointment 1 |
| Male | 39.1 | 42.1 |
| Female | 35.0 | 33.3 |

Partial healing (in %); this corresponds to at least 75% healing based on the total area of the genital warts.

| | Cream 1 | Ointment 1 |
| --- | --- | --- |
| Male | 43.5 | 63.2 |
| Female | 50.0 | 52.4 |

The results of the study show that a surprisingly high degree of complete healing, or partial healing, takes place as compared with the placebo values from similar studies using different formulations, in association with which the spontaneous regression of genital warts is approx. 20% in the case of women and approx. 5% in the case of men (Aldara™ (Imiquimod) Cream, 5% Product Monograph, marketed by 3M Pharmaceuticals, Northridge, Calif., Beutner K R et al.

(1998) J Am Acad Dermatol 38, 230-9, Edwards L et al. (1998) Arch Dermatol 134 (1); 25-30).

This therapeutic effect is attributed to the isopropyl myristate, an antiviral effect of which has consequently been demonstrated for the first time.

Clinical Study for Comparing an Ointment and a Cream Containing Isopropyl Myristate and Polyphenon® E 272 patients (equally divided between men and women in each case) took part in a multicenter clinical study which was carried out at a total of 30 different centers in Germany and Russia. The study was randomized and performed double-blind. The study examined the clinical efficacy of two different formulations of isopropyl myristate and Polyphenon® E (an ointment and a cream), as against the formulations from Example 1 containing isopropyl myristate, in the treatment of external genital warts.

The Polyphenon® E-containing formulations which were tested had the following compositions:

Cream 2:

| Substance | Quantity (in % w/w) |
| --- | --- |
| Polyphenon ® E | 10.000 |
| Cera alba | 5.263 |
| Monomuls | 2.105 |
| Lameform TGI | 4.211 |
| Cetiol V | 5.263 |
| Isopropyl myristate | 10.526 |
| Tocopherol | 0.526 |
| Controx KS | 0.050 |
| Glycerol | 5.263 |
| Disodium EDTA | 0.001 |
| Magnesium sulfate | 1.053 |
| D-Panthenol | 0.526 |
| Purified water | 55.213 |

Ointment 2:

| Substance | Quantity (in % w/w) |
| --- | --- |
| Polyphenon ® E | 15.000 |
| White Petrolatum, USP | 24.500 |
| White Wax, NF | 20.000 |
| Isopropyl Myristate, NF | 35.000 |
| Oleyl Alcohol, NF | 0.500 |
| Propylene Glycol Monostearate, NF | 5.000 |

The patients applied the topical study medication three times daily or until the genital warts had completely healed or for a maximum of twelve weeks.

During the study, the following data were collected:

| | Complete healing (in %) | | | |
| --- | --- | --- | --- | --- |
| | Cream 1 | Cream 2 | Ointment 1 | Ointment 2 |
| Male | 39.1 | 53.9 | 42.1 | 61.0 |
| Female | 35.0 | 39.5 | 33.3 | 56.8 |

| | Partial healing (≧75% in %) | | | |
| --- | --- | --- | --- | --- |
| | Cream 1 | Cream 2 | Ointment 1 | Ointment 2 |
| Male | 43.5 | 64.2 | 63.2 | 80.5 |
| Female | 50.0 | 47.4 | 52.4 | 81.1 |

Analysis of the study shows that, when comparing ointment 1 and cream 1, on the one hand, and ointment 2 and cream 2, on the other hand, the combination of isopropyl myristate and Polyphenon® E leads to a surprising increase in the efficacy of the pharmaceutical.

If the efficacy of ointment 2 is now compared with that of cream 2, it then becomes evident that ointment 2 is markedly more effective than cream 2. This suggests a synergistic effect between the Polyphenon® E and the isopropyl myristate in the hydrophobic ointment.

As a result of this synergistic effect, the individual active compounds in the formulation can, in order to achieve the same effect, be employed in substantially smaller quantities than the corresponding individual components. Consequently, the use of this synergistic formulation has advantages not only with regard to the effect but also with regard to the cost of preparing this formulation, something which in turn can have a positive effect on the cost of treating the patient.

The invention claimed is:

1. A pharmaceutical which comprises, as the pharmaceutically active compound, isopropyl myristate and a mixture of catechols comprising 4-15% (w/w) of (−)-epicatechol, 2-20% (w/w) of (−)-epicatechol gallate, 3-15% (w/w) of (−)-epigallocatechol, 40-75% (w/w) of (−)-epigallocatechol gallate, 0.1-1% (w/w) of (+)-gallocatechol and 1-10% (w/w) of (−)-gallocatechol gallate, and wherein the pharmaceutical comprises at least 5-50% (w/w) of isopropyl myristate.

2. A pharmaceutical as claimed in claim 1, characterized in that the pharmaceutical also comprises one or more additional pharmaceutical active compounds as a combination preparation for use which is simultaneous, separate or staggered in time.

3. A pharmaceutical as claimed in claim 2, characterized in that the additional pharmaceutical active compound is amphiphilic.

4. A pharmaceutical as claimed in claim 1, characterized in that said mixture of catechols comprises 10.8% (w/w) of (−)-epicatechol, 6.5% (w/w) of (−)-epicatechol gallate, 9.2% (w/w) of (−)-epigallocatechol, 54.8% (w/w) of (−)-epigallocatechol gallate and/or 4.0% (w/w) of (−)-gallocatechol gallate.

5. A pharmaceutical as claimed in claim 1, characterized in that said catechols are isolated from a tea extract.

6. A pharmaceutical as claimed in claim 1, characterized in that the formulation comprises 1-30% (w/w) of said mixture of catechols and at least 10-50% (w/w) of said isopropyl myristate.

7. A pharmaceutical as claimed in claim 1, which comprises further additives and/or auxiliary substances.

8. A pharmaceutical as claimed in claim 7, characterized in that the additives and/or auxiliary substances are hydrophobic and are preferably selected from petroleum jelly, wax, oleyl alcohol, propylene glycol monostearate and propylene glycol monopalmitostearate.

9. A pharmaceutical which comprises 35% (w/w) of isopropyl myristate, 15% (w/w) of a mixture of catechols comprising 4-15% (w/w) of (−)-epicatechol, 2-20% (w/w) of (−)-epicatechol gallate, 3-15% (w/w) of (−)-epigallocatechol, 40-75% (w/w) of (−)-epigallocatechol gallate, 0.1-1% (w/w) of (+)-gallocatechol and 1-10% (w/w) of (−)-gallocatechol gallate, 24.5% (w/w) of petroleum jelly, 20% (w/w) of wax, 5% (w/w) of propylene glycol mono stearate or propylene glycol monopalmitostearate and 0.5% (w/w) of oleyl alcohol.

10. A method of treating a papilloma virus-induced skin disease or benign tumor disease in a patient, said method comprising administering to a patient a pharmaceutical as claimed in claim 1.

11. The method as claimed in claim 10, characterized in that the papilloma virus-induced skin or tumor disease is caused by HPV 1, 2, 3, 4, 5, 6, 8, 9, 11, 12, 13, 14, 15, 16, 17, 18, 19-29, 31, 32, 34, 36-38, 46-50, 56 or 58.

12. The method as claimed in claim 10, characterized in that the papilloma virus-induced skin diseases are warts or genital warts and the papilloma virus-induced benign tumors are of the skin and/or mucosa.

13. The method as claimed in claim 10, characterized in that the pharmaceutical is applied topically.

14. The pharmaceutical as claimed in claim 1, wherein said mixture of catechols comprises 5-7% (w/w) of said (−)-epicatechol gallate.

15. The pharmaceutical as claimed in claim 1, wherein said mixture of catechols comprises 0.1-0.6% (w/w) of said (+)-gallocatechol.

16. The pharmaceutical as claimed in claim 1, wherein said mixture of catechols comprises 1-5% (w/w) of said (−)-gallocatechol gallate.

17. The pharmaceutical as claimed in claim 1, wherein said pharmaceutical comprises at least 10-50% (w/w) of said isopropyl myristate.

18. The pharmaceutical as claimed in claim 17, wherein said pharmaceutical comprises at least 25-50% (w/w) of said isopropyl myristate.

19. The pharmaceutical as claimed in claim 18, wherein said pharmaceutical comprises at least 35-50% (w/w) of said isopropyl myristate.

20. The pharmaceutical as claimed in claim 6, wherein said formulation comprises 2-20% (w/w) of said mixture of catechols.

21. The pharmaceutical as claimed in claim 20, wherein said formulation comprises 15-18% (w/w) of said mixture of catechols.

22. The pharmaceutical as claimed in claim 6, wherein said formulation comprises at least 25-60% (w/w) of said isopropyl myristate.

23. The pharmaceutical as claimed in claim 22, wherein said formulation comprises at least 35-50% (w/w) of said isopropyl myristate.

24. The method as claimed in claim 12, wherein said "papilloma virus-induced" benign tumors of the skin and/or mucosa are verrucae plantares, verrucae vulgares, verrucae planae juveniles, epidermodysplasia verruciformis, Condylomata acuminata, Condylomata plana, bowenoid papulosis, papillomas on the larynx and oral mucosa or focal epithelial hyperplasia.

25. The method as claimed in claim 13, wherein said pharmaceutical is applied genitally or vaginally.

* * * * *

UNITED STATES PATENT AND TRADEMARK OFFICE
CERTIFICATE OF CORRECTION

| | | |
|---|---|---|
| PATENT NO. | : 7,858,662 B2 | Page 1 of 1 |
| APPLICATION NO. | : 10/495889 | |
| DATED | : December 28, 2010 | |
| INVENTOR(S) | : Chang et al. | |

It is certified that error appears in the above-identified patent and that said Letters Patent is hereby corrected as shown below:

On the title page, item [75] Inventors, replace "Johanna Holldack, Ebeltoft (DK)" with --Johanna Holldack, Aarhus C (DK)--;

Under Foreign Application Priority Data, replace "101 56 794" with --101-56-794.4--.

Page 2, under OTHER PUBLICATIONS, in Bickers and Athar, replace "691695" with --691-695--.

Page 3, under OTHER PUBLICATIONS, in Office Action mailed on Jun. 17, 2008, replace "forU.S." with --for U.S.--.

Column 2, Lines 34-35, replace "a symptomatically" with --asymptomatically--.

Column 8, Line 67, replace "Beutner K R et al." with --Beutner KR et al.-- .

Signed and Sealed this
Twenty-fourth Day of January, 2012

David J. Kappos
*Director of the United States Patent and Trademark Office*